United States Patent
Murakami et al.

(10) Patent No.: US 11,571,368 B2
(45) Date of Patent: Feb. 7, 2023

(54) DENTAL POLYMERIZABLE COMPOSITION

(71) Applicant: GC Corporation, Shizuoka (JP)

(72) Inventors: Shogo Murakami, Tokyo (JP); Hiroaki Kakinuma, Tokyo (JP); Keita Sato, Tokyo (JP)

(73) Assignee: GC Corporation, Shizuoka (JP)

(*) Notice: Subject to any disclaimer, the term of this patent is extended or adjusted under 35 U.S.C. 154(b) by 105 days.

(21) Appl. No.: 17/190,703

(22) Filed: Mar. 3, 2021

(65) Prior Publication Data

US 2021/0299000 A1 Sep. 30, 2021

(30) Foreign Application Priority Data

Mar. 24, 2020 (JP) .............................. JP2020-053184

(51) Int. Cl.
- *A61K 6/889* (2020.01)
- *A61K 6/831* (2020.01)
- *A61K 6/62* (2020.01)

(52) U.S. Cl.
CPC ................ *A61K 6/889* (2020.01); *A61K 6/62* (2020.01); *A61K 6/831* (2020.01)

(58) Field of Classification Search
CPC ...................................................... A61K 6/61
See application file for complete search history.

(56) References Cited

U.S. PATENT DOCUMENTS

| | | |
|---|---|---|
| 2012/0059083 A1 | 3/2012 | Tokui et al. |
| 2016/0051450 A1* | 2/2016 | Kashiki ............... A61K 6/60 526/204 |

FOREIGN PATENT DOCUMENTS

| | | |
|---|---|---|
| EP | 2163234 | 3/2010 |
| EP | 3342393 | 7/2018 |
| JP | 2010-037324 | 2/2010 |
| JP | 2012-051856 | 3/2012 |

* cited by examiner

*Primary Examiner* — Michael F Pepitone
(74) *Attorney, Agent, or Firm* — IPUSA, PLLC

(57) ABSTRACT

A dental polymerizable composition includes: a first component containing a (meth)acrylate, a pentavalent vanadium compound, and a thiourea derivative; and a second component containing a (meth)acrylate and an organic peroxide.

3 Claims, No Drawings

DENTAL POLYMERIZABLE COMPOSITION

CROSS-REFERENCE TO RELATED APPLICATIONS

This application is based upon and claims priority to Japanese Patent Application No. 2020-053184, filed on Mar. 24, 2020, the entire contents of which are incorporated herein by reference.

FIELD OF THE INVENTION

The present invention relates to a dental polymerizable composition.

BACKGROUND OF THE INVENTION

Patent Document 1 discloses a polymerizable composition including, for example, a first component containing a (meth)acrylate, a thiourea derivative, a vanadium compound, and a second component containing a (meth)acrylate and an organic peroxide, wherein the polymerizable composition can be used under wet conditions, such as in an oral cavity, in a dental treatment.

RELATED-ART DOCUMENT

Patent Documents

Patent Document 1: Japanese Patent Application Laid-Open No. 2012-51856

SUMMARY OF THE INVENTION

Problems to be Solved by the Invention

However, there is a need to improve the curability of polymerizable compositions after long-term storage, that is, to improve the storage stability of polymerizable compositions.

One aspect of the invention is to provide a dental polymerizable composition having improved storage stability.

Means for Solving the Problems

One aspect of the invention is a dental polymerizable composition including: a first component containing a (meth)acrylate, a pentavalent vanadium compound, and a thiourea derivative; and a second component containing a (meth)acrylate and an organic peroxide.

Effects of the Invention

One aspect of the invention is to provide a dental polymerizable composition having improved storage stability.

DETAILED DESCRIPTION OF THE INVENTION

Next, an embodiment for carrying out the present invention will be described.

<Dental Polymerizable Composition>

A dental polymerizable composition of the present embodiment is a two-component dental polymerizable composition containing a first component including a (meth)acrylate, a pentavalent vanadium compound, and a thiourea derivative; and a second component including a (meth)acrylate and an organic peroxide.

Examples of forms of the first component and the second component include a paste and the like.

The mass ratio of the first component and the second component of the dental polymerizable composition of the present embodiment is typically within the range of from 10:1 to 1:10.

The dental polymerizable composition of the present embodiment is typically used by kneading the first and second components.

The dental polymerizable composition of the present embodiment can be applied to dental cements, desensitizers for hypersensitivity, dental sealants, and the like.

Hereinafter, components constituting a dental polymerizable composition of the present embodiment will be described.

<(meth)acrylate>

In the present specification and claims, (meth)acrylate refers to a compound (e.g., monomer, oligomer, prepolymer) having one or more methacryloyloxy groups and/or acryloyloxy groups (hereinafter referred to as (meth)acryloyloxy groups).

The (meth)acrylate may or may not have an acid group, but preferably the (meth)acrylate in the first component is (meth)acrylate free of an acid group. This improves the storage stability of the dental polymerizable composition of the present embodiment.

<(meth)acrylate Free of an Acid Group>

The (meth)acrylate free of an acid group preferably has two or more (meth)acryloyloxy groups.

Examples of the (meth)acrylates free of an acid group include methyl (meth)acrylate, ethyl (meth)acrylate, isopropyl (meth)acrylate, n-butyl (meth)acrylate, isobutyl (meth)acrylate, hydroxypropyl (meth)acrylate, tetrahydrofurfuryl (meth)acrylate, glycidyl (meth)acrylate, 2-hydroxyethyl (meth)acrylate, 2-hydroxypropyl (meth)acrylate, 3-hydroxypropyl (meth)acrylate, 2-methoxyethyl (meth)acrylate, 2-ethoxyethyl (meth)acrylate, 2-methylhexyl (meth)acrylate, 2-ethylhexyl (meth)acrylate, benzyl (meth)acrylate, 2-hydroxy-1,3-di(meth)acryloyloxypropane, ethyleneglycol di(meth)acrylate, diethyleneglycol di(meth)acrylate, triethyleneglycol di(meth)acrylate, butyleneglycol di(meth)acrylate, neopentylglycol di(meth)acrylate, 1,3-butanediol di(meth)acrylate, 1,4-butanediol di(meth)acrylate, 1,6-hexanediol di(meth)acrylate, trimethylolpropane tri(meth)acrylate, trimethylolethane tri(meth)acrylate, pentaerythritol tri(meth)acrylate, trimethylolmethane tri(meth)acrylate, pentaerythritol tetra(meth)acrylate, polybutyleneglycol di(meth)acrylate, bisphenol-A diglycidyl (meth)acrylate, di-2-(meth)acryloyloxyethyl-2,2,4-trimethylhexamethylene dicarbamate, 1,3,5-tris[1,3-bis{(meth)acryloyloxy}-2-propoxycarbonylaminohexane]-1,3,5-(1H,3H,5H)triazine-2,4,6-trione, 2,2-bis[4-(3-(meth)acryloyloxy-2-hydroxypropyl)phenyl]propane, N,N'-(2,2,4-trimethylhexamethylene)bis[2-(aminocarboxy)propane-1,3-diol]tetramethacrylate, and the like. Two or more kinds of (meth)acrylates free of an acid group may be used in combination. Among these, 2-hydroxy-1,3-di(meth)acryloyloxypropane, di-2-(meth)acryloyloxyethyl-2,2,4-trimethylhexamethylene dicarbamate, ethylene glycol di(meth)acrylate, neopentyl glycol di(meth)acrylate, and triethylene glycol di(meth)acrylate are preferably used in terms of the mechanical strength of the cured product of the dental polymerizable composition of the present embodiment.

The content of the (meth)acrylate free of an acid group in the dental polymerizable composition of the present embodiment is preferably 10 to 95% by mass and further preferably 15 to 80% by mass, improving the working time of the dental polymerizable composition of the present embodiment when the content of the (meth)acrylate in the dental polymerizable composition of the present embodiment is 10% by mass or more and 95% by mass or less.

<(meth)acrylate with Acid Group>

Examples of (meth)acrylates having acid groups include (meth)acrylate having a phosphate group, (meth)acrylate having a pyrophosphate group, (meth)acrylate having a thiophosphate group, (meth)acrylate having a carboxyl group, (meth)acrylate having a sulfonic acid group, (meth)acrylate having a phosphonic acid group, (meth)acrylate having a phosphonic acid group, and the like. Two or more kinds of (meth)acrylates may be used in combination. Among these, (meth)acrylate having a phosphate group or a thiophosphate group is preferably used in terms of solubility or teeth decalcification of the smear layer on the teeth surface of the dental polymerizable composition of the present embodiment, and particularly adhesion to the enamel.

The (meth)acrylate having an acid group may have multiple acid groups.

Alternatively, acid chlorides, alkali metal salts, and amine salts of (meth)acrylates with acid groups may be used instead of (meth)acrylates with acid groups.

Examples of the (meth)acrylates having a phosphate group include 2-(meth)acryloyloxyethyldihydrogenphosphate, bis[2-(meth)acryloyloxyethyl]hydrogenphosphate, 2-(meth)acryloyloxyethylphenyl hydrogenphosphate, 6-(meth)acryloyloxyhexyldihydrogenphosphate, 6-(meth)acryloyloxyhexylphenyl hydrogenphosphate, 10-(meth)acryloyloxydecyldihydrogenphosphate, 1,3-di(meth)acryloylpropan-2-dihydrogenphosphate, 1,3-di(meth)acryloylpropan-2-phenylhydrogenphosphate, bis[5-{2-(meth)acryloyloxyethoxycarbonyl}heptyl] hydrogenphosphate, and the like. Among these, 10-(meth)acryloyloxydecyldihydrogenphosphate is preferably used in terms of adhesion of the dental polymerizable composition of the present embodiment.

Examples of the (meth)acrylates having pyrophosphate groups include bis(2-(meth)acryloyloxyethyl) pyrophosphate, bis(4-(meth)acryloyloxybutyl) pyrophosphate, bis(6-(meth)acryloyloxyhexyl) pyrophosphate, bis(8-(meth)acryloyloxyoctyl) pyrophosphate, bis(10-(meth)acryloyloxydecyl) pyrophosphate, and the like.

Examples of the (meth)acrylates having thiophosphate groups include 2-(meth)acryloyloxyethyl dihydrothiophosphate, 3-(meth)acryloyloxypropyl dihydrogenthiophosphate, 4-(meth)acryloyloxybutyl dihydrogenthiophosphate, 5-(meth)acryloyloxypentyl dihydrogenthiophosphate, 6-(meth)acryloyloxyhexyl dihydrogenthiophosphate, 7-(meth)acryloyloxyoxyheptyl dihydrogenthiophosphate, 8-(meth)acryloyloxyoctyl dihydrogenthiophosphate, 9-(meth)acryloyloxynonyl dihydrogenthiophosphate, 10-(meth)acryloyloxydecyl dihydrogenthiophosphate, 11-(meth)acryloyloxyundecyl dihydrogenthiophosphate, 12-(meth)acryloyloxydodecyl dihydrogenthiophosphate, 13-(meth)acryloyloxytridecyl dihydrogenthiophosphate, 14-(meth)acryloyloxytetradecyl dihydrogenthiophosphate, 15-(meth)acryloyloxypentadecyl dihydrogenthiophosphate, 16-(meth)acryloyloxyhexadecyl dihydrogenthiophosphate, 17-(meth)acryloyloxyheptadecyl dihydrogenthiophosphate, 18-(meth)acryloyloxyoctadecyl dihydrogenthiophosphate, 19-(meth)acryloyloxynonadecyl dihydrogenthiophosphate, 20-(meth)acryloyloxyicosyl dihydrogenthiophosphate, and the like.

Examples of the (meth)acrylates having carboxyl groups include, for example, 4-(meth)acryloyloxyethyl trimellitic acid, 4-(meth)acryloyloxyethyl trimellitic anhydride, 4-(meth)acryloyloxy decyltrimellitic acid, 4-(meth)acryloyloxydecyltrimellitic anhydride, 11-(meth)acryloyloxy-1,1-undecarboxylic acid, 1,4-di(meth)acryloyloxy pyromellitic acid, 2-(meth)acryloyloxyethylmaleic acid, 2-(meth)acryloyloxyethyl phthalic acid, 2-(meth)acryloyloxyethyl hexahydrophthalic acid, and the like.

Examples of the (meth)acrylates having sulfonic acid groups include 2-(meth)acrylamide-2-methylpropanesulfonic acid, styrenesulfonic acid, 2-sulfoethyl (meth)acrylate, and the like.

Examples of the (meth)acrylates having phosphonic acid groups include 2-(meth)acryloyloxyethylphenylphosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexyl-3-phosphonoacetate, 10-(meth)acryloyloxydecyl-3-phosphonoacetate, and the like.

The content of the (meth)acrylate having an acid group in the dental polymerizable composition of the present embodiment is preferably 0.1 to 20% by mass and further preferably 0.5 to 10% by mass. When the content of (meth)acrylate having an acid group in the dental polymerizable composition of the present embodiment is 0.1% by mass or more, improving the adhesion of the dental polymerizable composition of the present embodiment to tooth. When the content of (meth)acrylate having an acid group in the dental polymerizable composition of the present embodiment is 20% by mass or less, further improving the curability of the dental polymerizable composition of the present embodiment.

<Pentavalent Vanadium Compound>

A pentavalent vanadium compound functions as a polymerization accelerator.

The pentavalent vanadium compound is preferably soluble in (meth)acrylate.

The pentavalent vanadium compound is preferably an organic vanadium compound. This enhances the solubility of pentavalent vanadium compounds in the dental polymerizable composition of the present embodiment with respect to (meth)acrylates.

The pentavalent vanadium compound is preferably vanadium oxytrialkoxide. This improves the storage stability of the dental polymerizable composition of the present embodiment.

Examples of the vanadium oxytrialkoxides include vanadium oxytriisopropoxide, vanadium oxytripropoxide, vanadium oxytriethoxide, and the like.

Examples of pentavalent vanadium compounds other than vanadium trialkoxides include, for example, vanadium oxychloride and the like.

The pentavalent vanadium compound may be used alone, or two or more kinds of pentavalent vanadium compounds may be used in combination.

The content of the pentavalent vanadium compound in the dental polymerizable compositions of the present embodiment is preferably from 0.001 to 1% by mass and more preferably from 0.01 to 0.1% by mass. When the content of the pentavalent vanadium compound in the dental polymerizable composition of the present embodiment is 0.001% by mass or more, improving the curability of the dental polymerizable composition of the present embodiment. When the content of the pentavalent vanadium compound in the dental polymerizable composition of the present embodiment is 1% by mass or less, improving the storage stability of the dental polymerizable composition of the present embodiment.

Also, for the same reason as above, a content of the pentavalent vanadium compound in a first component is preferably 0.002 to 2% by mass and further preferably 0.02 to 0.2% by mass.

<Thiourea Derivatives>

A thiourea derivative functions as a reducing agent of a chemical polymerization initiator.

Examples of the thiourea derivatives include ethylene thiourea, N-methylthiourea, N-ethylthiourea, N-propylthiourea, N-butylthiourea, N-lauryl thiourea, N-phenylthiourea, N-cyclohexylthiourea, N,N-dimethyl thiourea, N,N-diethylthiourea, N,N-dipropylthiourea, N,N-dibutylthiourea, N,N-dilauryl thiourea, N,N-diphenylthiourea, N,N-dicyclohexylthiourea, trimethylthiourea, tetramethyl thiourea, N-acetylthiourea, N-benzoyl thiourea, 1-allyl-3-(2-hydroxyethyl)-2-thiourea, 1-(2-tetrahydrofurfuryl)-2-thiourea, N-tert-butyl-N'-isopropylthiourea, 2-pyridylthiourea, and the like. Two or more kinds of thiourea derivatives may be used in combination. Among these, N-benzoyl thiourea is preferably used in terms of curability of the dental polymerizable composition of the present embodiment.

The content of the thiourea derivative in the dental polymerizable composition of the present embodiment is preferably 0.1 to 5% by mass and further preferably 0.1 to 1% by mass. When the content of the thiourea derivative in the dental polymerizable composition of the present embodiment is 0.1% by mass or more, improving the curability of the dental polymerizable composition of the present embodiment. When the content of the thiourea derivative in the dental polymerizable composition of the present embodiment is 5% by mass or less, improving the solubility of the thiourea derivative in the dental polymerizable composition of the present embodiment with respect to (meth)acrylate.

Also, for the same reason as above, a content of the thiourea derivative in the first component is preferably 0.2 to 10% by mass and further preferably 0.2 to 2% by mass.

<Organic Peroxides>

An organic peroxide functions as an oxidizer of a chemical polymerization initiator.

Examples of the organic peroxides include benzoyl peroxide, cumene hydroperoxide, t-butyl hydroperoxide, t-amyl hydroperoxide, 1,1,3,3-tetramethylbutyl hydroperoxide, 2,5-dimethyl-2,5-di(hydroperoxy)hexane, p-diisopropylbenzene monohydroperoxide, p-methane hydroperoxide, pinane hydroperoxide, and the like. Two or more kinds of organic peroxides may be used in combination. Among these, cumene hydroperoxide is preferably used in terms of curability of the dental polymerizable composition of the present embodiment.

The content of the organic peroxide in the dental polymerizable composition of the present embodiment is preferably 0.01 to 5% by mass and further preferably 0.1 to 2% by mass. When the content of the organic peroxide in the dental polymerizable composition of the present embodiment is 0.01% by mass or more, improving the curability of the dental polymerizable composition of the present embodiment. When the content of the organic peroxide in the dental polymerizable composition of the present embodiment is 5% by mass or less, increases the working time with the dental polymerizable composition of the present embodiment, thereby ensuring sufficient working time.

For the same reason as above, a content of the organic peroxide in a second component is preferably 0.02 to 10% by mass and further preferably 0.2 to 4% by mass.

<Other Components>

The first component may further contain a tertiary amine.

The tertiary amine functions as a reducing agent in a chemical polymerization initiator.

The tertiary amine may be either a tertiary aliphatic amine or a tertiary aromatic amine, but is preferably a tertiary aromatic amine, particularly alkyl p-dialkylaminobenzoate.

The tertiary aliphatic amines include, for example, N,N-dimethylaminoethylmethacrylate, triethanolamine, and the like.

Examples of the alkyl p-dialkylaminobenzoates include methyl p-dimethylaminobenzoate, ethyl p-dimethylaminobenzoate, propyl p-dimethylaminobenzoate, amyl p-dimethylaminobenzoate, isoamyl p-dimethylaminobenzoate, ethyl p-diethylaminobenzoate, propyl p-diethylaminobenzoate, and the like.

Examples of tertiary aromatic amines other than the alkyl p-dialkylaminobenzoate include 7-dimethylamino-4-methylcoumarin, N,N-dimethylaniline, N,N-dibenzylaniline, N,N-dimethyl-p-toluidine, N,N-diethyl-p-toluidine, N,N-bis (2-hydroxyethyl)-p-toluidine, N,N,2,4,6-N,N,2,4-tetramethylaniline, N,N-diethyl-2,4,6-trimethylaniline, and the like.

The tertiary amine may be used alone or in combination with two or more kinds.

The first and/or second components may further contain a polymerization inhibitor, a photopolymerization initiator, a filler, and the like.

Examples of the polymerization inhibitors include dibutyl hydroxytoluene, 6-tert-butyl-2,4-xylenol, 2,6-di-tert-butyl-p-cresol, and the like. Two or more kinds of polymerization inhibitors may be used in combination.

Examples of the photopolymerization initiators include camphorquinone, phenylbis (2,4,6-trimethylbenzoyl) phosphineoxide, 2,4,6-trimethylbenzoyl diphenylphosphine, benzyl ketal, diacetyl ketal, benzyl dimethyl ketal, benzyl diethyl ketal, benzyl bis(2-methoxyethyl) ketal, 4,4'-dimethyl (benzyl dimethyl ketal), anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropylthioxanthone, 2-nitrothioxanthone, 2-methylthioxanthone, 2,4-dimethylthioxanthone, 2,4-diethylthioxanthone, 2,4-diisopropylthioxanthone, 2-chloro-7-trifluoromethylthioxanthone, thioxanthone-10,10-dioxide, thioxanthone-10-oxide, benzoin methyl ether, benzoin ethyl ether, benzoin isopropyl ether, benzoin isobutyl ether, benzophenone, bis(4-dimethylaminophenyl)ketone, 4,4'-bis(diethylamino)benzophenone, and the like. Two or more kinds of photopolymerization initiators may be used in combination.

Examples of the fillers include anhydrous silicic acid powder, fumed silica, alumina powder, glass powder (e.g., barium glass powder, fluoroaluminosilicate glass powder), and the like. Two or more kinds of fillers may be used in combination.

The filler may be treated with a surface treatment agent such as a silane coupling agent and the like.

The content of the filler in the dental polymerizable composition of the present embodiment is preferably 4 to 90% by mass and further preferably 15 to 80% by mass. When the content of the filler in the dental polymerizable composition of the present embodiment is 4% by mass or more, improving the mechanical strength of the cured product of the dental polymerizable composition of the present embodiment. When the content of the filler in the dental polymerizable composition of the present embodiment is 90% by mass or less, improving the working time of the dental polymerizable composition of the present embodiment.

EXAMPLES

Hereinafter, examples of the present invention will be described, but the present invention is not limited to the examples.

Examples 1 to 9, Comparative Examples 1 to 3

(Preparation of Paste 1)

A paste 1 was prepared by mixing methacrylate free of an acid group, a pentavalent vanadium compound, a thiourea derivative, a filler, a tertiary amine, a photopolymerization initiator, and a polymerization inhibitor according to the amounts [% by mass] indicated in Table 1.

(Preparation of Paste 2)

A paste 2 was prepared by mixing methacrylate free of an acid group, methacrylate having an acid group, an organic peroxide, a filler, and a polymerization inhibitor according to the amounts [% by mass] indicated in Table 1.

The abbreviations indicated in Table 1 are as follows.
Bis-GMA: 2,2-bis[4-(3-methacryloyloxy-2-hydroxypropyl)phenyl]propane
UDMA: di-2-methacryloyloxyethyl-2,2,4-trimethylhexamethylene dicarbamate
EBDMA: Ethoxylated bisphenol-A dimethacrylate
NPG: Neopentylglycol dimethacrylate
TEGDMA: Triethylene glycol dimethacrylate
MDP: 10-methacryloyloxydecyldihydrogenphosphate
HOMS: 2-methacryloyloxyethylsuccinic acid
TIPOVO: vanadium oxytriisopropoxide
TPOVO: vanadium oxytripropoxide
TEOVO: vanadium oxytriethoxide
VAA: vanadyl acetylacetonate (bis(2,4-pentanedionate)vanadium (IV) oxide)
NBTU: N-benzoyl thiourea
CHP: cumene hydroperoxide
Filler 1: barium glass powder G018-053 UF0.4 (manufactured by SCHOTT)
Filler 2: aerosil RX300 (hydrophobic fumed silica) (manufactured by Nippon Aerosil Co., Ltd.)
Filler 3: anhydrous silicate powder RAF1000 (manufactured by Tatsumori)
EPA: ethyl p-dimethylaminobenzoate
CQ: camphorquinone
BHT: dibutyl hydroxytoluene The storage stability of pastes 1 and 2 (dental polymerizable compositions) was then evaluated.

(Storage Stability)

Accelerated testing was performed to evaluate the storage stability of dental polymerizable compositions. Specifically, the pastes 1 and 2 were stored at 60° C. for 14 days. Next, the pastes 1 and 2 before and after storage were kneaded at a mass ratio of 1:1, and the setting time was measured to evaluate the storage stability of the dental polymerizable compositions in accordance with ISO4049:2019. Specifically, the setting time was determined by filling an acrylic ring having an inner diameter of 8 mm and a thickness of 2 mm with the kneaded pastes 1 and 2, and by measuring the temperature using an infrared radiation thermometer.

The criteria for storage stability are as follows.
Excellent: The change in the setting time of the dental polymerizable composition before and after storage is 3 minutes or less.
Good: The change in the setting time of the dental polymerizable composition before and after storage greater than 3 minutes, but 4 minutes or less.
Poor: The change in the setting time of the dental polymerizable composition before and after storage greater than 4 minutes.

Tables 1 and 2 indicate the evaluation results of the storage stability of dental polymerizable compositions.

TABLE 1

| | | | Examples | | | | | |
|---|---|---|---|---|---|---|---|---|
| | | | 1 | 2 | 3 | 4 | 5 | 6 |
| Paste 1 | Methacrylate without an acid group | Bis-GMA | 6.5 | | | | | |
| | | UDMA | | 20 | 13 | 20 | 20 | 13 |
| | | EBDMA | 20 | 6.5 | 13 | 6.5 | 6.5 | 13 |
| | | NPG | 6.5 | 6.5 | 7 | 6.5 | 6.5 | 7 |
| | Vanadium compound | TIPOVO | 0.03 | 0.03 | 0.03 | 0.02 | 0.015 | |
| | | TPOVO | | | | | | 0.03 |
| | | TEOVO | | | | | | |
| | | VAA | | | | | | |
| | Thiourea derivative | NBTU | 1 | 1 | 1 | 1 | 1 | 1 |
| | Filler | Filler 1 | 64.77 | 64.77 | 64.77 | 64.78 | 64.78 | 64.77 |
| | | Filler 2 | 1 | 1 | 1 | 1 | 1 | 1 |
| | Tertiary amine | EPA | 0.05 | 0.05 | 0.05 | 0.05 | 0.05 | 0.05 |
| | Photopolymerization initiator | CQ | 0.1 | 0.1 | 0.1 | 0.1 | 0.1 | 0.1 |
| | Polymerization inhibitor | BHT | 0.05 | 0.05 | 0.05 | 0.05 | 0.05 | 0.05 |
| | Total | | 100 | 100 | 100 | 100 | 100 | 100 |
| Paste 2 | Methacrylate without an acid | EBDMA | 16 | 16 | 16 | 16 | 16 | 16 |
| | | TEGDMA | 16 | 16 | 16 | 16 | 16 | 16 |
| | Methacrylate having an acid | MDP | | | | | | |
| | | HOMS | | | | | | |

TABLE 1-continued

|  |  |  | Examples | | | | | |
| --- | --- | --- | --- | --- | --- | --- | --- | --- |
|  |  |  | 1 | 2 | 3 | 4 | 5 | 6 |
|  | Organic peroxide | CHP | 1.5 | 1.5 | 1.5 | 1.5 | 1.5 | 1.5 |
|  | Filler | Filler 1 | 65.35 | 65.35 | 65.35 | 65.35 | 65.35 | 65.35 |
|  |  | Filler 2 | 1 | 1 | 1 | 1 | 1 | 1 |
|  |  | Filler 3 |  |  |  |  |  |  |
|  | Polymerization inhibitor | BHT | 0.15 | 0.15 | 0.15 | 0.15 | 0.15 | 0.15 |
|  | Total |  | 100 | 100 | 100 | 100 | 100 | 100 |
| Storage stability | Setting time before storage |  | 9'19" | 10'48" | 9'36" | 9'56" | 10'42" | 9'45" |
|  | Setting time after storage |  | 12'19" | 14'12" | 12'35" | 13'32" | 13'38" | 12'44" |
|  | Evaluation |  | Excellent | Good | Excellent | Good | Excellent | Excellent |

TABLE 2

|  |  |  | Examples | | | Comparative Examples | | |
| --- | --- | --- | --- | --- | --- | --- | --- | --- |
|  |  |  | 7 | 8 | 9 | 1 | 2 | 3 |
| Paste 1 | Methacrylate without an acid group | Bis-GMA |  |  |  | 6.5 |  |  |
|  |  | UDMA | 13 | 13 | 13 |  | 20 | 13 |
|  |  | EBDMA | 13 | 13 | 13 | 20 | 6.5 | 13 |
|  |  | NPG | 7 | 7 | 7 | 6.5 | 6.5 | 7 |
|  | Vanadium compound | TIPOVO |  | 0.03 | 0.03 |  |  |  |
|  |  | TPOVO |  |  |  |  |  |  |
|  |  | TEOVO | 0.03 |  |  |  |  |  |
|  |  | VAA |  |  |  | 0.03 | 0.03 | 0.03 |
|  | Thiourea derivative | NBTU | 1 | 1 | 1 | 1 | 1 | 1 |
|  | Filler | Filler 1 | 64.77 | 64.77 | 64.77 | 64.77 | 64.77 | 64.77 |
|  |  | Filler 2 | 1 | 1 | 1 | 1 | 1 | 1 |
|  | Tertiary amine | EPA | 0.05 | 0.05 | 0.05 | 0.05 | 0.05 | 0.05 |
|  | Photopolymerization initiator | CQ | 0.1 | 0.1 | 0.1 | 0.1 | 0.1 | 0.1 |
|  | Polymerization inhibitor | BHT | 0.05 | 0.05 | 0.05 | 0.05 | 0.05 | 0.05 |
|  | Total |  | 100 | 100 | 100 | 100 | 100 | 100 |
| Paste 2 | Methacrylate without an acid | EBDMA | 16 | 15.5 | 15.5 | 16 | 16 | 16 |
|  |  | TEGDMA | 16 | 15.5 | 15.5 | 16 | 16 | 16 |
|  | Methacrylate having an acid | MDP |  | 1 |  |  |  |  |
|  |  | HOMS |  |  | 1 |  |  |  |
|  | Organic peroxide | CHP | 1.5 | 1.5 | 1.5 | 1.5 | 1.5 | 1.5 |
|  | Filler | Filler 1 | 65.35 |  | 65.35 | 65.35 | 65.35 | 65.35 |
|  |  | Filler 2 | 1 | 1 | 1 | 1 | 1 | 1 |
|  |  | Filler 3 |  | 65.35 |  |  |  |  |
|  | Polymerization inhibitor | BHT | 0.15 | 0.15 | 0.15 | 0.15 | 0.15 | 0.15 |
|  | Total |  | 100 | 100 | 100 | 100 | 100 | 100 |
| Storage stability | Setting time before storage |  | 9'23" | 5'49" | 6'49" | 5'53" | 1'53" | 1'53" |
|  | Setting time after storage |  | 12'20" | 7'37" | 9'27" | 11'02" | 13'51" | 15'20" |
|  | Evaluation |  | Excellent | Excellent | Excellent | Poor | Poor | Poor |

From Tables 1 and 2, it can be seen that the dental polymerizable compositions of Examples 1 to 9 have high storage stability.

In contrast, the dental polymerizable compositions of Comparative Examples 1 to 3 have a paste 1 which does not contain a pentavalent vanadium compound but contains a tetravalent vanadyl acetylacetonate. Accordingly, the dental polymerizable compositions of Comparative Examples 1 to 3 have low storage stability.

What is claimed is:

1. A dental polymerizable composition comprising:
a first component containing a (meth)acrylate, a pentavalent vanadium compound, and a thiourea derivative; and
a second component containing a (meth)acrylate and an organic peroxide,
wherein, the thiourea derivative is at least one selected from ethylene thiourea, N-methylthiourea, N-ethylthiourea, N-propylthiourea, N-butylthiourea, N-lauryl thiourea, N-phenylthiourea, N-cyclohexylthiourea, N,N-dimethyl thiourea, N,N-diethylthiourea, N,N-dipropylthiourea, N,N-dibutylthiourea, N,N-dilauryl thiourea, N,N-diphenylthiourea, N,N-dicyclohexylthiourea, trimethylthiourea, tetramethyl thiourea, N-acetylthiourea, N-benzoyl thiourea, 1-allyl-3-(2-hydroxyethyl)-2-thiourea, 1-(2-tetrahydrofurfuryl)-2-thiourea, N-tert-butyl-N'-isopropylthiourea, and 2-pyridylthiourea.

2. The dental polymerizable composition according to claim 1, wherein the pentavalent vanadium compound is an organic vanadium compound.

3. The dental polymerizable composition according to claim 2, wherein the pentavalent vanadium compound is a vanadium oxytrialkoxide.

\* \* \* \* \*